(12) United States Patent
Saxena et al.

(10) Patent No.: US 8,772,367 B2
(45) Date of Patent: Jul. 8, 2014

(54) SILOXANE MONOMERS CONTAINING HYDROLYSIS RESISTANCE CARBOSILOXANE LINKAGE, PROCESS FOR THEIR PREPARATION AND THIN FILMS CONTAINING THE SAME FOR CONTACT LENS APPLICATION

(75) Inventors: Anubhav Saxena, Bangalore (IN); Umapathy Senthilkumar, Bangalore (IN); Kenrick M. Lewis, Flushing, NY (US)

(73) Assignee: Momentive Performance Materials Inc., Waterford, NY (US)

(*) Notice: Subject to any disclaimer, the term of this patent is extended or adjusted under 35 U.S.C. 154(b) by 474 days.

(21) Appl. No.: 13/052,306

(22) Filed: Mar. 21, 2011

(65) Prior Publication Data

US 2012/0245249 A1   Sep. 27, 2012

(51) Int. Cl.
*C08F 290/06* (2006.01)
*C07F 7/02* (2006.01)
*C07F 7/08* (2006.01)
*C07F 7/10* (2006.01)

(52) U.S. Cl.
USPC ........... 523/107; 556/400; 556/431; 556/434; 556/436; 556/437; 556/438; 556/439; 556/465; 556/482

(58) Field of Classification Search
USPC .......... 523/107; 556/400, 431, 434, 436, 437, 556/438, 439, 465, 482
See application file for complete search history.

(56) References Cited

U.S. PATENT DOCUMENTS

| | | | |
|---|---|---|---|
| 3,377,371 A | 4/1968 | Quaal | |
| 3,408,429 A | 10/1968 | Wichterle | |
| 3,496,254 A | 2/1970 | Wichterle | |
| 3,808,178 A | 4/1974 | Gaylord | |
| 4,084,459 A | 4/1978 | Clark | |
| 4,197,266 A | 4/1980 | Clark | |
| 4,259,467 A | 3/1981 | Keogh et al. | |
| 4,260,725 A | 4/1981 | Keogh et al. | |
| 4,433,125 A * | 2/1984 | Ichinohe et al. | 526/279 |
| 4,954,587 A | 9/1990 | Mueller | |
| 5,010,141 A | 4/1991 | Mueller | |
| 5,079,319 A | 1/1992 | Mueller | |
| 5,115,056 A | 5/1992 | Mueller | |
| 5,260,000 A | 11/1993 | Nandy | |
| 5,336,797 A | 8/1994 | McGee et al. | |
| 5,358,995 A | 10/1994 | Lai et al. | |
| 5,387,632 A | 2/1995 | Lai et al. | |
| 5,451,617 A | 9/1995 | Lai et al. | |
| 5,486,579 A | 1/1996 | Lai et al. | |
| 5,986,122 A | 11/1999 | Lewis et al. | |
| 5,998,498 A | 12/1999 | Vanderlaan et al. | |
| 7,259,220 B1 | 8/2007 | Farris et al. | |
| 7,507,775 B2 | 3/2009 | Leatherman | |
| 7,700,797 B2 | 4/2010 | Leatherman et al. | |
| 2008/0081894 A1 | 4/2008 | Fujisawa et al. | |
| 2010/0069279 A1 | 3/2010 | Leatherman et al. | |
| 2011/0009658 A1 | 1/2011 | Awasthi et al. | |

FOREIGN PATENT DOCUMENTS

| | | |
|---|---|---|
| EP | 0131911 A1 | 1/1985 |
| GB | 2119951 A | 11/1983 |
| JP | 63-295611 A | 12/1968 |
| WO | 86/01219 A1 | 2/1986 |

OTHER PUBLICATIONS

Efimov Y T et al., "Synthesis of Organosilicon Derivatives of Acrylic Acids", Journal of General Chemistry of the USSR, vol. 61, No. 10, Part 2, 1991, pp. 2003-2901.

Stern, et al (J. Polymer Science Part B: Polymer Physics 25 (1987) 1263-1298.

\* cited by examiner

*Primary Examiner* — Michael Pepitone
(74) *Attorney, Agent, or Firm* — Dominick G. Vicari

(57) ABSTRACT

There is provided new mono-(meth)acrylate functionalized silicone monomers containing carbosiloxane linkage for improved hydrolysis resistance, useful in making water absorbing silicone-hydrogel films for contact lens applications. This invention also provides homo-polymers and copolymers made from the mono-(meth)acrylate functionalized hydrophilic silicone monomers described herein. Also provided is a process for producing the monomers and polymers described herein and contact lenses produced from the same.

7 Claims, No Drawings

SILOXANE MONOMERS CONTAINING HYDROLYSIS RESISTANCE CARBOSILOXANE LINKAGE, PROCESS FOR THEIR PREPARATION AND THIN FILMS CONTAINING THE SAME FOR CONTACT LENS APPLICATION

FIELD OF THE INVENTION

The present invention relates to mono-acrylate functional silicone monomers comprising hydrolytically stable carbosiloxane linkages and polymers thereof. The present invention is also directed to hydrogel compositions useful for the production of biomedical devices, particularly soft contact lenses characterized by high oxygen permeability, high water content, low protein denaturation behavior and strong resistance to hydrolysis across a range of pH and temperature ranges.

BACKGROUND OF THE INVENTION

Any publications or references discussed herein are presented to describe the background of the invention and to provide additional detail regarding its practice. Nothing herein is to be construed as an admission that the inventors are not entitled to antedate such disclosure by virtue of prior invention.

Silicone-hydrogel films are used to make extended wear soft contact lenses due to their high oxygen permeability, flexibility, comfort and reduced corneal complications. Conventional hydrogel materials (e.g. HEMA), by themselves have poor oxygen permeability and they transport oxygen to the eye through the absorbed water molecules. Water itself has a low Dk value (80 barrer). 1 Barrer=$10^{-11}$ (cm$^3$ O$_2$) cm cm$^{-2}$ s$^{-1}$ mmHg$^{-1}$ where 'cm$^3$ O$_2$' is at a quantity of oxygen at standard temperature and pressure and where 'cm' represents the thickness of the material and cm$^{-2}$ is the reciprocal of the surface area of that material. Lenses made from conventional hydrogel materials, upon exposure to atmospheric air for long periods, get slowly dehydrated and the amount of oxygen transported to the cornea is reduced, which leads to eye irritation, redness and other corneal complications, all of which restrict their use for extended periods of wear.

Silicone-hydrogels with the comfort of soft contact lenses and significantly higher oxygen permeability overcame these obstacles for extended wear and were revolutionary in the field of ophthalmic lenses. The following patents describe silicone-hydrogels for use in extended wear contacts all of which are incorporated herein in their entirety by reference. U.S. Pat. Nos. 4,954,587; 5,010,141; 5,079,319; 5,115,056; 5,260,000; 5,336,797; 5,358,995; 5,387,632; 5,451,617; 5,486,579 and 5,998,498.

U.S. Pat. No. 3,808,178 claims compositions prepared by copolymerization of a poly-siloxanylalkyl acrylic ester and an alkyl acrylic ester for the production of contact lenses with increased oxygen permeability. The compositions disclosed (see Columns 2 and 3) have trisiloxane (Si—O—Si—O—Si) and siloxycarbo (Si—O—C) linkages, which are susceptible to hydrolysis in spite of the presence of sterically hindered groups attached to silicon.

The polymer obtained by copolymerizing 3-[tris(trimethylsiloxy)silyl]propyl methacrylate (usually abbreviated TRIS), [(CH$_3$)$_3$SiO]$_3$Si(CH$_2$)$_3$OOCC(CH$_3$)=CH$_2$, and N,N-dimethylacrylamide, H$_2$C=CHCON(CH$_3$)$_2$, is disclosed in U.S. Pat. Nos. 5,358,995 and 5,387,632, both of which are incorporated herein in their entirety by reference, as a hydrogel composition useful for preparing ophthalmic lenses with good wettability and oxygen permeability. However, if a carboxylic acid such as methacrylic acid is included in the copolymerization to improve the water content of the product, the composition is gradually hydrolyzed and contact lenses made from it degrade when stored in aqueous media. U.S. Pat. No. 3,377,371 and US 2008/0081894 A1, both of which are incorporated herein in their entirety by reference, disclose use of sterically hindered derivatives of TRIS to forestall this type of degradation. However, the continued presence of siloxycarbo (Si—O—C—) and/or trisiloxane (Si—O—Si—O—Si) units in the compositions makes them susceptible to hydrolysis. U.S. Pat. No. 4,260,725 and U.S. Pat. No. 4,259,467, both of which are incorporated herein in their entirety by reference, disclose hydrolytically stable contact lens comprising polysiloxane-containing hydrophilic side chains. The disclosed polysiloxane monomers are bifunctional in nature and have —Si—C linkages instead of —Si—O—C— bonds in terminal positions. However, in the lens industry mono-functional monomers are preferred more than multi-functional monomers as they give better control of the modulus of the final lens material. The instant invention discloses mono-functional monomers comprising carbosiloxane linkages (for example, Si—CH$_2$CH$_2$—Si and Si—CH$_2$—CH$_2$—Si—O—Si) to avoid the material degradation problems attendant to hydrolysis, while at the same time providing better surface wettability and oxygen permeability to films, lenses and other objects made from said monomers.

Carbosiloxanes contain both the —Si(CHR)$_x$—Si— and —Si—O—Si— functionalities. R is hydrogen or a hydrocarbyl group such as an alkyl, cycloalkyl or aryl group. The subscript x is an integer greater than or equal to 1. Use of carbosiloxanes to impart hydrolysis resistance to surfactants in agricultural and other topical formulations is disclosed in U.S. Pat. Nos. 7,700,797 B2 and 7,507,775 B2, both of which are incorporated herein in their entirety by reference. The instant invention discloses the acrylate and methacrylated carbosiloxane monomers, having improved hydrolysis resistance, that can be copolymerized with unsaturated hydrophilic monomers, such as N-vinyl pyrrolidone and N,N-dimethylacrylamide, to produce silicone hydrogels suitable for ophthalmic lenses.

In their study of gas permeability through silicone polymer membranes, Stern, et al (J. Polymer Science Part B: Polymer Physics 25 (1987) 1263-1298) reported that substitution of methyl groups by bulky groups (e.g., ethyl, isopropyl, butyl, hexyl) on the silicone backbone, or the replacement of siloxane (—SiOSi—) linkage by carbosilane (—Si(CH$_2$)$_n$Si—) linkage resulted in reduced oxygen permeability. Based on Stern et al report, one would expect the oxygen permeability to get reduced when siloxane linkage (—Si—O—Si) is replaced by carbosiloxane linkage (—Si(CH$_2$)$_n$Si—) in the backbone chain. Surprisingly, the silicone hydrogel film produced using the carbosiloxane monomer of the current invention showed improved oxygen permeability in comparison to the corresponding siloxane monomer having conventional siloxane linkage.

The instant invention provides carbosiloxane monomers and polymers derived there from that satisfy the deficiencies that exist in current state-of-the-art products and technologies.

SUMMARY OF THE INVENTION

An object of the present invention is to provide a silicone monomer having the following general formulae (I):

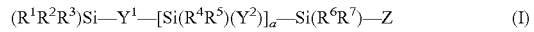

wherein a is 0 to about 100; $Y^1$ is a substituted or unsubstituted divalent alkyl linking group of 1 to about 10 carbon atoms; $Y^2$ is a substituted or unsubstituted divalent alkyl linking group of 1 to about 10 carbon atoms or a divalent hetero atom; $R^1$, $R^2$, $R^3$, $R^4$, $R^5$, $R^6$, and $R^7$ are independently selected from the group consisting of monovalent aliphatic, cycloaliphatic or aromatic hydrocarbon groups of 1 to about 10 carbons and halogenated hydrocarbon groups of 1 to about 10 carbons, —$Y^2$—Si($R^8R^9R^{10}$) and A, wherein $R^8R^9R^{10}$ are independently selected from the group consisting of monovalent aliphatic, cycloaliphatic and aromatic hydrocarbon groups of 1 to about 10 carbons; A is a monovalent hydrophilic or hydrophobic moiety selected from the group consisting of substituted or unsubstituted, saturated and unsaturated aliphatic, cycloaliphatic or aromatic hydrocarbons and substituted or unsubstituted, saturated and unsaturated aliphatic, cycloaliphatic or aromatic hydrocarbons containing hetero atoms;

Z has the following general formulae (II)

$$—R^{11}—B—X \qquad (II)$$

wherein $R^{11}$ is a linear or branched, divalent alkyl linking group having 0 to about 20 carbon atoms; B is a divalent hydrophilic or hydrophobic moiety selected from the group consisting of substituted or unsubstituted, saturated and unsaturated aliphatic, cycloaliphatic or aromatic hydrocarbons and substituted or unsubstituted, saturated and unsaturated aliphatic, cycloaliphatic or aromatic hydrocarbons containing hetero atoms; and X is acrylamide or a polymerizable group having the following general formula (III)

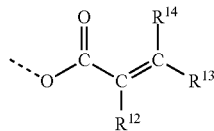

(III)

wherein $R^{12}$, $R^{13}$, and $R^{14}$ is hydrogen or a substituted or unsubstituted saturated monovalent hydrocarbon group of 1 to about 20 carbons.

Another object of the present invention is to provide homo and copolymers derived from the described monomers and silicone hydrogels containing the same.

Still another object of the present invention is to provide soft, flexible, transparent, water absorbing, inherently wettable and better oxygen permeable contact lens comprising the silicone-hydrogel film of the present invention.

Still yet another object of the present invention is to a process for producing a silicone monomer having the general following formulae (IV):

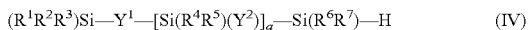

$$(R^1R^2R^3)Si—Y^1—[Si(R^4R^5)(Y^2)]_a—Si(R^6R^7)—H \qquad (IV)$$

wherein a is 0 to 100; $Y^1$ is a substituted or unsubstituted divalent alkyl linking group of 1 to 10 carbon atoms; $Y^2$ is a substituted or unsubstituted divalent alkyl linking group of 1 to about 10 carbon atoms or a divalent hetero atom; $R^1$, $R^2$, $R^3$, $R^4$, $R^5$, $R^6$, and $R^7$ is independently selected from the group consisting of monovalent aliphatic, cycloaliphatic or aromatic hydrocarbon groups of 1 to about 10 carbons and halogenated hydrocarbon groups of 1 to about 10 carbons, —$Y^2$—Si($R^8R^9R^{10}$) and A, wherein $R^8R^9R^{10}$ are independently selected from the group consisting of monovalent aliphatic, cycloaliphatic and aromatic hydrocarbon groups of 1 to about 10 carbons; A is a monovalent hydrophilic or hydrophobic moiety selected from the group consisting of substituted or unsubstituted, saturated and unsaturated aliphatic, cycloaliphatic or cycloaromatic hydrocarbons and substituted or unsubstituted, saturated and unsaturated aliphatic, cycloaliphatic or aromatic hydrocarbons containing hetero atoms; This is reacted with terminally unsaturated group having the general formula (V):

$$R^{15}—B-M \qquad (V)$$

wherein $R^{15}$ is selected from the group consisting of linear or branched unsaturated alkyl groups having 0 to about 20 carbon atoms, B is a divalent hydrophilic or hydrophobic moiety selected from the group consisting of substituted or unsubstituted, saturated and unsaturated aliphatic, cycloaliphatic or aromatic hydrocarbons and substituted or unsubstituted, saturated and unsaturated aliphatic, cycloaliphatic or aromatic hydrocarbons containing hetero atoms. "A" and "B" comprises functionalities selected from the group consisting of alkyl, alcohol, ether, ester, amide, amine, acid and its salts, cyano, thio, urethane, urea, sulfonate, sulphonamide, phosphate and combinations thereof. "M" in formulae V is selected from the group consisting of hydroxyl, halogen, epoxy and carboxylic acid group to produce functionalized carbosiloxane. Once the functionalized carbosiloxane is produced it is reacted with an alkylacryloyl compound having the following formula (VI):

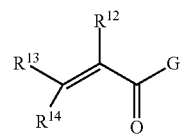

(VI)

wherein G is selected from the group consisting of a halogen, hydroxyl and alkyloxy having 1 to about 10 carbon atoms and $R^{12}$, $R^{13}$ and $R^{14}$ is independently selected from the group consisting of hydrogen, substituted saturated monovalent hydrocarbons having 1 to about 20 carbons and unsubstituted saturated monovalent hydrocarbons having 1 to about 20 carbons to produce said silicone monomer set forth herein above.

The present invention is further described in the detailed description section including the examples provided below.

DETAILED DESCRIPTION OF THE INVENTION

In accordance with the present invention, mono-acrylate and methacrylate functionalized carbosiloxane monomers that are non-bulky, show improved hydrolysis resistance and useful for preparing silicone-hydrogel films for contact lens applications are disclosed. Carbosiloxane monomer of the present invention showed improved hydrolysis resistance under acidic and basic pH conditions in comparison to the corresponding conventional siloxane monomers. Silicone hydrogel films obtained with these monomers also showed better oxygen permeability, surface wettability and low modulus in comparison to films of the corresponding conventional siloxane monomers.

In the present invention, the monomers disclosed have a carbosilane linkage, —Si—(CH$_2$)$_n$—Si—, which makes it possible to produce hydrolytically stable (hydrolysis resistance) monomers and polymers. It also produces silicone hydrogel film with improved oxygen permeability in comparison to corresponding conventional siloxane monomer.

The silicone—hydrogel film of the present invention also provides better surface wettability without any secondary surface treatment, like plasma oxidation or plasma coating, or internal wetting agents. That is, the contact lenses produced from silicone-hydrogel films of the present invention, without secondary treatment, are soft, flexible and inherently wettable with high oxygen permeability. The monomers of the present invention also allow for miscibility with hydrophilic organic comonomers without the need for any solvent and the silicone hydrogels thus produced are transparent in entire range of compositions.

As used herein, "homopolymers" are polymers made from the same repeating monomer and 'copolymers" are polymers wherein the polymer contains at least two structurally different monomers. Notations such as (meth)acrylate denote monomer with either acrylate or methacrylate functionality.

Also, as used in the specification and including the appended claims, the singular forms "a," "an," and "the" include the plural, and reference to a particular numerical value includes at least that particular value, unless the context clearly dictates otherwise.

Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

All methods described herein may be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, "comprising," "including," "containing," "characterized by," and grammatical equivalents thereof are inclusive or open-ended terms that do not exclude additional, unrecited elements or method steps, but will also be understood to include the more restrictive terms "consisting of" and "consisting essentially of."

The monomers of the present invention can be used to obtain cured elastomer sheets with desirable physical strength and resistance to tearing after absorption of water. The (meth)acrylate functionalized silicone monomers/polymers of the present invention and their preparation and use in contact lens are further described in the sections below.

The present invention also provides silicone-hydrogel compositions comprising (meth)acrylated carbosiloxane monomers and conventional monomers such as HEMA or other contact lens monomers to produce soft, flexible water absorbing films. The homo and copolymers of the present invention are clear (no haze from poor miscibility) polymers that absorb water, have excellent surface wettability and oxygen permeability, which are necessary for the better comfort and good health of the human cornea. The present invention also provides contact lenses made from the silicone-hydrogel films of the claimed invention. These embodiments are further described below.

The silicone monomers having carbosilane linkage, —Si—$(CH_2)_n$—Si—, produced in the current invention may be used to form homo/copolymers that produce hydrolytically stable silicone-hydrogel films. The film shows inherent wettability and better oxygen permeability in comparison to films with conventional siloxane monomers. The contact lenses produced from the silicone-hydrogel films of the present invention do not require any expensive secondary treatments, like plasma oxidation or plasma coating, or internal wetting agents to improve wettability. That is, the contact lenses produced from silicone-hydrogel films of the present invention, without secondary treatment, are soft, flexible and inherently wettable with high oxygen permeability.

The mono-acrylate functional carbosiloxane monomers of the present invention have the general structure shown in formula (I):

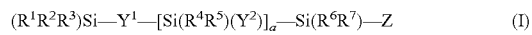

$(R^1R^2R^3)Si-Y^1-[Si(R^4R^5)(Y^2)]_a-Si(R^6R^7)-Z$      (I)

One of the preferred variants of the formula (I) of the present invention is the mono acrylate functional monomer having the general formula as shown below.

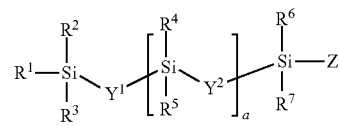

wherein a is 0 to 100; $Y^1$ is a substituted or unsubstituted divalent alkyl linking group of 1 to 10 carbon atoms, and $Y^2$ can be the same as $Y^1$ or a hetero atom such as nitrogen, oxygen or sulfur. $R^1$ to $R^7$ is independently selected from the group consisting of monovalent aliphatic, cycloaliphatic or aromatic hydrocarbon groups of 1 to about 10 carbons and halogenated hydrocarbon groups of 1 to about 10 carbons. $R^1$-$R^7$ can also be independently selected from —$Y^2$—Si$(R^8R^9R^{10})$ and A, where $R^8$ to $R^{10}$ is independently selected from the group consisting of monovalent aliphatic, cycloaliphatic or aromatic hydrocarbon groups of 1 to about 10 carbons and halogenated hydrocarbon groups of 1 to about 10 carbons. A can be a monovalent hydrophilic or hydrophobic moiety selected from the group consisting of, substituted or unsubstituted, saturated and unsaturated aliphatic, cycloaliphatic or aromatic hydrocarbons and optionally contains hetero atoms. Preferably, A comprises functionalities such as alkyl, alcohol, ether, ester, amide, amine, acid and its salts, cyano, thio, urethane, urea, carbonate, carbamate, sulfonate, sulphonamide, phosphate and their combinations.

Z in the above structure can have the general formula (II) shown below

—$R^{11}$—B—X      (II)

wherein $R^{11}$ is a linear or branched, divalent alkyl linking group having about 0 to about 20 carbon atoms.

B in general formula (II) is a divalent moiety selected from the group consisting of, substituted or unsubstituted, saturated and unsaturated aliphatic, cycloaliphatic or aromatic hydrocarbons and substituted or unsubstituted, saturated and unsaturated aliphatic, cycloaliphatic or aromatic hydrocarbons containing hetero atoms; Preferably, B comprises functionalities such as alcohols, ethers, esters, amides, amines, acids and its salts, cyano, thio, urethane, urea, carbonate, carbamate, sulfonates, sulphonamides, phosphates and their combinations.

In particular, some of the representative functionalities for B are shown below:

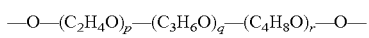

Polyether
wherein p and q are independently 0 to about 100; r is 0 to about 50 and (p+q+r) is greater than 0,

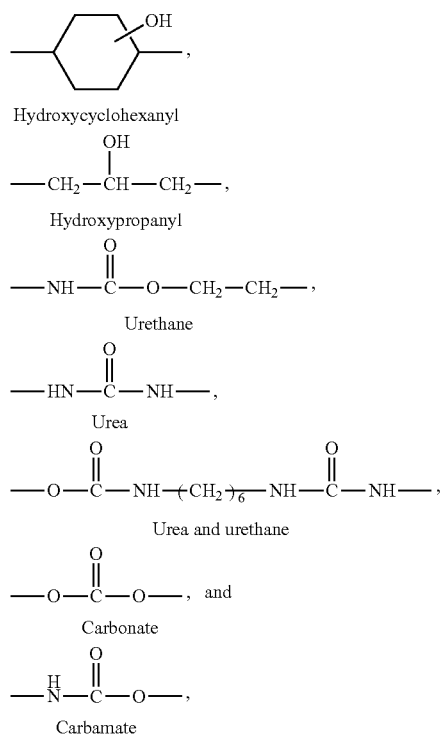

X is acrylamide or a polymerizable group having the general formula (III)

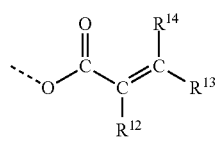

wherein $R^{12}$ to $R^{14}$ can be selected from hydrogen or a substituted or unsubstituted saturated monovalent hydrocarbon group of 1 to about 20 carbons.

The present invention is also directed to polymers formed by the reaction products of the monomers provided herein. These polymers may be homopolymers of one of the monomers of the present invention or copolymers of two structurally different silicone monomers of the present invention, and/or copolymers of one or more silicone monomers of the present invention and at least one other hydrophilic unsaturated organic monomers suitable for use in silicone hydrogels, with preferred non-limiting examples of such being N,N-dimethylacrylamide, 2-hydroxy-ethyl-methacrylate (HEMA), N-vinylpyrrolidone, and methacrylic acid. In such copolymers, the ratio of the silicone monomers of the present invention to the other hydrophilic unsaturated organic monomers is from about 1:100 to about 100:1 and preferably from about 20:80 to about 90:10 and more preferably from about 30:70 to about 80:20.

The unsaturated organic monomers and the carbosiloxane monomers of this invention are mutually miscible and form homogeneous mixtures. The use of compatibilizing solvents is not necessary. The carbosiloxane monomers of this invention are also either water-soluble or water-dispersible. Water-soluble carbosiloxane monomers are miscible with water to yield homogeneous solutions. Water-dispersible carbosiloxane monomers do not dissolve completely in water. Cloudiness, haze, colloid formation and similar visible signs of heterogeneity in the aqueous mixture are indicative of dispersion rather than solution. Both water solubility and water dispersibility are desirable features of the carbosiloxane monomers of the instant invention. When the carbosiloxane monomers contain a methacrylated ethoxylated polyether segment, water dispersibility is observed when the polyether content is less than about 60 weight percent of the total molecular weight, and water solubility when the polyether segment is greater than about 60 weight percent.

To form polymers using the monomers of the present invention, the desired monomers are mixed and the resulting mixture is polymerized and cured to form transparent thin films by known thermal techniques using free radical or cationic or anionic initiators and UV cure techniques using photoinitiators in the presence of crosslinking agents. The monomers added to the reaction mixture to form the polymers may be monomers or prepolymers. A "prepolymer" is a reaction intermediate polymer of medium molecular weight having polymerizable groups. Thus, it is understood that the terms "silicone-containing monomers" and "hydrophilic monomers" include prepolymers. The present invention is also directed to silicone hydrogel films comprising the homopolymers or copolymers detailed above.

One preferred variant of silicone monomer from structure (I) of the present invention has the following formula

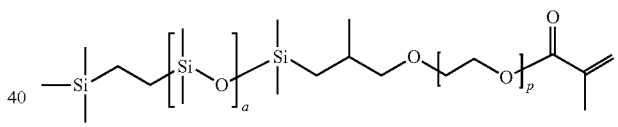

wherein B is a divalent polyether as shown in the representative example with p is 0 to about 100, preferably 2 to about 15, more preferably about 8, and q and r equals to 0; $Y^1$ is a divalent alkyl-linking group of about 1 to 10 carbons, preferably 1 to about 5 carbons, more preferably about 2 carbons. $Y^2$ is a combination of divalent heteroatom and divalent alkyl group and X is polymerizable methacrylate group. a is 0 to about 100, more preferably 0 to 20 inclusive, and even more preferably 1. Each of the R groups in the general monomer structure (I) is a monovalent alkyl-linking group, preferably a methyl group. $R^1$ to $R^7$ can also be selected from —$Y^2$—Si($R^8R^9R^{10}$) and A.

Another preferred variant of silicone monomer from structure (I) of the present invention has the following formula

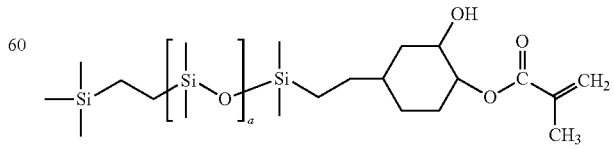

wherein B is a divalent hydroxyl containing cycloaliphatic ring; X is polymerizable methacrylate group, a is 0 to about 100, more preferably 0 to about 20 inclusive, and even more preferably 1. $Y^1$ is a divalent alkyl-linking group of about 1 to 10 carbons, preferably 1 to about 5 carbons, more preferably about 2 carbons. $Y^2$ is a combination of divalent heteroatom and divalent alkyl group. Each of the R groups in the general monomer structure (I) is a monovalent alkyl-linking group, preferably a methyl group. $R^1$ to $R^7$ can also be selected from $-Y^2-Si(R^8R^9R^{10})$ and A.

Another preferred variant of silicone monomer from structure (I) of the present invention has the following formula

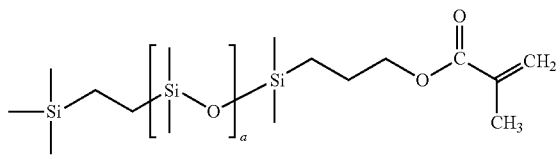

wherein B is a divalent alkyl group; X is polymerizable methacrylate group, a is 0 to about 100, more preferably 0 to about 20 inclusive, and even more preferably 1. Y' is a divalent alkyl-linking group of about 1 to 10 carbons, preferably 1 to about 5 carbons, more preferably about 2 carbons. $Y^2$ is a combination of divalent heteroatom and divalent alkyl group. Each of the R groups in the general monomer structure (I) is a monovalent alkyl-linking group, preferably a methyl group. $R^1$ to $R^7$ can also be selected from $-Y^2-Si(R^8R^9R^{10})$ and A.

Another embodiment of the present invention is directed to a process for producing the described silicone monomers comprising chemically reacting a silicone-containing compound having the general formula shown below $$(R^1R^2R^3)Si-Y^1-[Si(R^4R^5)(Y^2)]_a-Si(R^6R^7)-H \qquad (I)$$

wherein a is 0 to 100; $Y^1$ is a substituted or unsubstituted divalent alkyl linking group of 1 to 10 carbon atoms, and $Y^2$ can be $Y^1$ or a divalent hetero atom. $R^1$ to $R^7$ is independently selected from the group consisting of monovalent aliphatic, cycloaliphatic or aromatic hydrocarbon groups of 1 to about 10 carbons and halogenated hydrocarbon groups of 1 to about 10 carbons. Also, $R^1$-$R^7$ can be $-Y^2-Si(R^8R^9R^{10})$ and A, wherein $R^8$ to $R^{10}$ is independently selected from the group consisting of monovalent aliphatic, cycloaliphatic or aromatic hydrocarbon groups of 1 to about 10 carbons and halogenated hydrocarbon groups of 1 to about 10 carbons. A can be a monovalent hydrophilic or hydrophobic moiety selected from the group consisting of, substituted or unsubstituted, saturated and unsaturated aliphatic, cycloaliphatic or aromatic hydrocarbons and optionally contains hetero atoms. Once produced it is reacted with terminally unsaturated group having the general formula as shown below (II)

$$R^{15}-B-M \qquad (II)$$

wherein $R^{15}$ is a linear or branched unsaturated alkyl group having about 0 to about 20 carbon atoms, B is divalent moiety selected from the group consisting of substituted or unsubstituted, saturated and unsaturated aliphatic, cycloaliphatic or aromatic hydrocarbons and substituted or unsubstituted, saturated and unsaturated aliphatic, cycloaliphatic or aromatic hydrocarbons containing hetero atoms; Preferably, B comprises functionalities such as alcohols, ethers, esters, amides, amines, acids and its salts, cyano, thio, urethane, urea, carbonate, carbamate, sulfonates, sulphonamides, phosphates and their combinations. M can be hydroxyl or halogen or epoxy or carboxylic acid group.

Once the functionalized carbosiloxane is produced it is reacted with an alkylacryloyl compound having the general formula (IV).

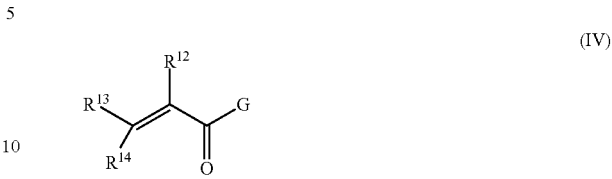

wherein G can be a halogen or hydroxyl or alkyloxy having 1 to 10 carbon atoms. $R^{12}$ to $R^{14}$ can be selected from hydrogen or a substituted or unsubstituted saturated monovalent hydrocarbon group of 1 to about 20 carbons to produce said silicone monomer. The reaction of the functionalized carbosiloxane with alkylacryloyl compound having the general formula (IV) can be carried out in the presence of a tertiary amine base or basic ion-exchange resin (IER) or azeotrope forming solvent or reactant. The azeotrope forming solvent can be selected from hexane, heptane, toluene etc. and the reactant such as methylmethacrylate under the inert reaction conditions.

In another embodiment, the monomer of the present invention can be used to form silicone-hydrogels for contact lens applications, via processes known in the art. Accordingly, the present invention is also directed to contact lenses produced from either homo or copolymers of the present invention. The monomers/polymers of the present invention can be formed into contact lenses by spin casting processes, as disclosed in U.S. Pat. Nos. 3,408,429 and 3,496,254, cast molding processes, as disclosed in U.S. Pat. Nos. 4,084,459 and 4,197,266, combinations of methods thereof, or any other known method for making contact lenses in which all of the aforementioned references are incorporated herein. Polymerization may be conducted either in a spinning mold, or a stationary mold corresponding to a desired contact lens shape and thickness. The lens may be further subjected to mechanical finishing, as occasion demands. Polymerization may also be conducted in an appropriate mold or vessel to form buttons, plates or rods, which may then be processed (e.g., cut or polished via lathe or laser) to give a contact lens having a desired shape.

In another embodiment, the silicone hydrogel compositions of the present invention form clear, transparent homogeneous single-phase solution that can be cured directly without employing any compatibilizing solvents. Conventional silicone-hydrogel films are generally produced by curing a mixture of hydrophobic silicone monomers and hydrophilic hydrogel monomers in the presence of about 10 to 40 wt. % of solvent, as they are incompatible with each other. However in the current invention, the inventive methacrylated carbosiloxane monomers are found to be miscible with conventional hydrophilic hydrogel monomers (such as HEMA) and can form homogeneous solutions suitable to produce silicone-hydrogel films without employing any solvent.

In another embodiment, the silicone hydrogel composition of the present invention can be cured to form silicone-hydrogels for contact lens applications using moulds that have either hydrophilic or hydrophobic surfaces and their combinations. The silicone hydrogel film made from the inventive monomers can be released from the mould and purified from the leachable using either water or organic solvents, such as isopropyl alcohol, or the combinations of water and organic solvents.

In another embodiment of the present invention, the silicone-hydrogel films of the present invention are soft, flexible, and highly transparent and water absorbing. Silicone-hydrogel films made from the inventive monomers exhibit better hydrolytic stability with better oxygen permeability compared to ones made using conventional silicone monomers. The present silicone hydrogel films were found to have dynamic contact angles with water, less than 80° and absorb about 10 to about 70 wt. % of water, which can vary depending on the silicone hydrogel composition. The silicone hydrogels produced were also found to have good mechanical properties required for the contact lens application.

In another embodiment, the carbosiloxane monomers of the present invention show better hydrolytic stability under acidic and basic conditions in comparison to the corresponding siloxanes.

The polymers of the present invention may also contain ultraviolet absorbents, antimicrobial agents, pigments, colorants and bioactive molecules in the form of additives or comonomers.

As stated above, the silicone-hydrogels of the present invention are oxygen transporting with improved surface wettable properties when compared to silicone monomers having bulky alkyl groups. The monomers and prepolymers employed in accordance with this invention are readily polymerized to form three-dimensional networks, which permit the transport of oxygen with improved wettability along with better mechanicals and optical clarity.

Specific use of the films include intraocular contact lenses, artificial corneas, daily disposable and extended wearable contact lenses or as coatings for biomedical devices.

EXAMPLES

The following examples are illustrative only and should not be construed as limiting the invention, which is properly delineated in the appended claims. Carbosiloxane monomers having different hydrophilic moieties with polymerizable functionality were produced. The hydrolytic stability of these novel monomers were measured under basic, neutral and acidic pH conditions and showed improved hydrolytic stability compared to conventional silicone monomers with same functionality. The carbosiloxane monomers were further copolymerized with conventional hydrogel monomers or mixtures thereof with different weight ratios to produce silicone hydrogel films. The films obtained with monomers of the current invention were also found to have better oxygen permeability, inherent wettability and lower modulus that are key for the contact lens application.

The silicone-hydrogel films produced were evaluated for lens properties using the following methods.

(1) Equilibrium Water Content

The film was immersed in deionized water for 48 hours then the surface water was wiped off gently using lintless tissue paper. The hydrated film was weighed precisely and then dried in an oven at 37° C. for 48 hours and weighed again for dry weight. Water content was calculated based on weight change using the following equation.

$$\% \text{ Water content} = \frac{\text{Weight of hydrated lens} - \text{Weight of dry lens}}{\text{Weight of hydrated lens}} \times 100$$

(2) Water Wettability

Water wettability of the film surface was evaluated by measuring contact angle using a captive air bubble method with a Ramé Hart NRL C.A. goniometer. In the captive bubble method, to better simulate the on eye conditions, an air bubble injected from a syringe is brought into contact with the film immersed in milli-Q water and the contact angle is then measured. Lower contact angle values represent a greater degree of hydrophilicity or better surface wettability of the film.

(3) Oxygen Permeability (Dk Value)

Oxygen permeability is one of the important factors in contact lenses and generally the higher the permeability the more desirable the lens. The oxygen permeability (Dk) for these samples was measured using a polarographic technique following ISO 9913 standard method. The film was clamped into the permeation cell and the donor chamber was filled with oxygen saturated PBS (phosphate buffered saline). The concentration of oxygen in the receptor cell was monitored, as a function of time, and the permeability was determined from the slope of concentration vs time plot.

(4) Modulus

The Young's modulus of the hydrated film was measured using an Instron tensile tester. The wet samples were cut into 6 cm×0.8 cm strips and the mechanical properties were measured with a load cell of 50 N and crosshead speed of 10 mm/minute. The modulus was determined from the initial slope of a stress-strain curve. Modulus is directly correlated to the softness of the material. Lower the modulus, softer is the material.

Monomer Preparation

Example 1 (Ex. 1)

Synthesis of Compound Represented by the Formula

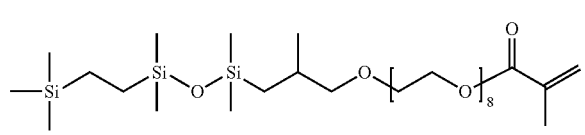

This monomer was prepared using two-step process. In the first step, a hydrosilylation reaction occurs between hydroxyl terminated methallyl polyether and mono-hydride functional carbosiloxane. In the second step, the hydroxyl group is converted into polymerizable methacrylate group through a methacrylation reaction. The mono-hydride functional carbosiloxane was prepared using the process disclosed in U.S. Pat. No. 7,259,220 B1, which is herein incorporated in its entirety by reference.

In a specific process, 1-(2-trimethylsilylethyl)-1,1,3,3-tetramethyldisiloxane (25 g), a hydride functional carbosiloxane, and a methallyl-terminated polyethylene glycol (46 g), having an average of 8 ethylene oxide (EO) units in the chain, were introduced into 250 mL three-neck round bottom (RB) flask equipped with a reflux condenser, mechanical stirrer, temperature controller with thermocouple and a nitrogen inlet. The contents were heated to 80° C. to 90° C. in presence of Karstedt's catalyst (50 to 100 ppm of Pt with respect to total reactant charge) and buffer (U.S. Pat. No. 5,986,122) to prevent side reactions like dehydrocoupling reaction from taking place. After completion of the hydrosilylation, volatile compounds were removed from the reaction product under reduced pressure. The final product, hydroxyl terminated carbosiloxane polyether, was obtained as a colorless, transparent liquid in quantitative yield without any undesired side products. The resultant pure product was well characterized by multinuclear NMR spectroscopy. Synthesis of the silicone polyethers of the present invention can occur with or without solvent. If solvents are used, preferred ones include toluene, isopropylalcohol or methyl ethyl ketone.

H-NMR (ppm): 0.02 ($Si(CH_3)$, 0.3 & 0.6 ($SiCH_2CH$), 0.4 ($SiCH_2CH_2Si$), 1.0 ($Si(CH_3)$, 1.9 (—$CH<$), 3.2 & 3.3 (>$CH$—$CH_2$—$O$—), 3.6 (—$CH_2CH_2O$—).

Si—NMR (ppm): 3.4 ($Si(CH_3)_3CH_2$), 7.2 ($O$—$Si(CH_3)_2(CH_2)$), 8.5 ($O$—$Si(CH_3)_2(CH_2CH_2)$).

Next, the carbosiloxane polyether that was synthesized in the step above, triethylamine (11.3 g) and methylethylketone (100 ml) were introduced into three-neck one liter RB flask equipped with dropping funnel and a stirring blade. The flask was immersed in an ice bath and methacryloyl chloride (11.2 g) was added drop wise using dropping funnel over a period of approximately 1 hour with constant stirring. After completion of the addition the stirring was continued for another 3 hours at room temperature. The triethylamine hydrochloride salt that precipitated out during the reaction was filtered off. The solvent was removed with a rotary vacuum evaporator and the final monomer was obtained as colorless to pale yellow, transparent liquid. The low boiling point of the solvent used enables the solvent to be removed completely at a temperature of about 30° C. to 40° C. under vacuum (i.e. less than about 10 mm Hg). The resulting monomer was well characterized by infrared spectroscopy, multinuclear NMR spectroscopy.

H-NMR (ppm): 0.02 ($Si(CH_3)$, 0.3 & 0.6 ($SiCH_2CH$), 0.4 ($SiCH_2CH_2Si$), 0.98 ($Si(CH_3)$, 1.98 ($CH_3$), 3.1 & 3.3 (>$CH$—$CH_2$—$O$—), 3.64 (—$CH_2CH_2O$—), 4.2 ($CH_2COO$), 5.6 & 6.15 ($CH_2=$).

Si—NMR (ppm): 3.5 ($Si(CH_3)_3CH_2$), 7.2 ($O$—$Si(CH_3)_2(CH_2)$), 8.4 ($O$—$Si(CH_3)_2(CH_2CH_2)$).

Example 2 (Ex. 2)

Synthesis of Compound Represented by the Formula

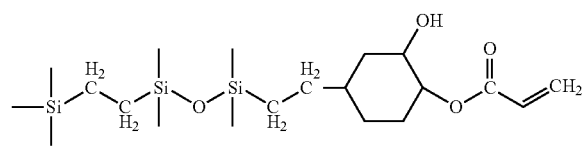 [SMILES: C=CC(=O)OC1CCC(CC[Si](C)(C)O[Si](C)(C)CC[Si](C)(C)C)CC1O]

This monomer was prepared was also prepared using two-step process. In the first step, a hydrosilylation reaction occurs between hydride functional carbosiloxane and vinyl functional cyclohexene epoxide. In the second step, the epoxide group is reacted with unsaturated acids to introduce polymerizable group in it.

In a specific process, 1-(2-trimethylsilylethyl)-1,1,3,3-tetramethyldisiloxane (25 g) and vinyl cyclohexene epoxide (13.2 g) were introduced into 250 mL three-neck round bottom (RB) flask equipped with a reflux condenser, mechanical stirrer, temperature controller with thermocouple and a nitrogen inlet. The contents were heated to 80° C. to 90° C. in presence of Karstedt's catalyst (10 to 50 ppm Pt with respect to total reactant charge) and buffer (U.S. Pat. No. 5,986,122) to prevent side reactions like dehydrocoupling reaction from taking place. After completion of the hydrosilylation, distilling out unwanted volatile compounds under reduced pressure purified the reaction product. The final product, epoxy functional carbosiloxane, was obtained as colorless, transparent liquid in quantitative yield without any undesired side products. The resultant pure product was well characterized by proton NMR spectroscopy. The epoxy functional carbosiloxane of the present invention can occur with or without solvent. If solvents are used, preferred ones include toluene, isopropylalcohol or methyl ethyl ketone.

H-NMR (ppm): 0.02 ($Si(CH_3)$, 0.4 ($SiCH_2CH_2Si$), 0.5 ($SiCH_2$), 1.2 to 2 ($CH_2$).

Next, the epoxy functional carbosiloxane synthesized above, titanium isopropoxide (0.4 wt % with respect to carbosiloxane) and hydroquinone (0.0025 wt % with respect to carbosiloxane) were introduced into three-neck one liter RB flask equipped with dropping funnel and a stirring blade. The flask was heated to 90 deg C. in an oil bath and then acrylic acid (7.68 g) was added in a drop wise manner into the RB with constant stirring. After completion of the addition the stirring was continued for another 5 hours at 90 deg C. The solvent (toluene) and other volatile impurities were removed with a rotary vacuum evaporator and the final monomer was obtained as colorless, transparent liquid. The resulting monoacrylated carbosiloxane monomer was well characterized by infrared spectroscopy, proton NMR spectroscopy.

H-NMR (ppm): 0.02 ($Si(CH_3)$, 0.4 ($SiCH_2CH_2Si$), 0.5 ($SiCH_2$), 1.2 to 2 ($CH_2$), 3.8 & 4.8 ($CH_2$), 5.8, 6.2 & 6.4 ($CH_2=CH$—).

Formation of Silicone-Hydrogel Films

Example 3 (Ex. 3)

The compound obtained in Example 1 (49 parts by weight), 2-hydroxy ethyl methacrylate (49 parts by weight), ethylene glycol dimethacrylate (EGDMA) (1 part by weight), and benzoyl peroxide (1 part by weight) were mixed and stirred. The resulting clear, homogeneous and transparent reaction mixture was purged with nitrogen gas and poured into a polyethylene terephthalate mould. The thin film of the reaction mixture was thermally cured using hot air oven at 85° C. for 8 hours. After curing, heating the film in 10% isopropyl alcohol (IPA), in deionized (DI) water, released it from the mould and purified from the leachables. The film was further washed with hot DI water. The final silicone hydrogel film thus produced was soft, flexible and transparent and stored in DI water and measured for some of the contact lens properties. Table 1 shows the details of the formulation and the properties of the silicone hydrogel films produced.

Examples 4 (Ex. 4)

A silicone-hydrogel film was obtained in the same way as in Example 3 except that the compound obtained in Example 2 was used instead of compound obtained in Example 1. The final sample was obtained as clear, transparent thin film and stored in pure water.

Comparative Example 1 (CEx. 1)

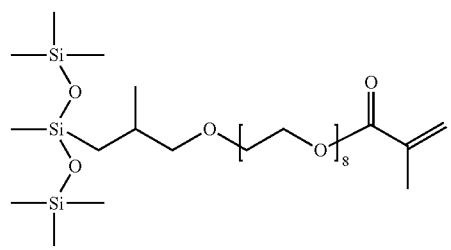

The monomer was prepared in the same way as in Example 1 except that 1,1,1,3,5,5,5-heptamethyltrisiloxane was used instead of 1-(2-trimethylsilylethyl)-1,1,3,3-tetramethyldisiloxane. The mono-acrylated siloxane monomer produced was well characterized by infrared spectroscopy, multinuclear NMR spectroscopy.

H-NMR (ppm): 0.02 (Si(CH$_3$), 0.3 & 0.6 (SiCH$_2$CH), 0.98 (Si(CH$_3$), 1.98 (CH$_3$), 3.1 & 3.3 (>CH—CH$_2$—O—), 3.64 (—CH$_2$CH$_2$O—), 4.3 (CH$_2$COO), 5.6 & 6.15 (CH$_2$=).

Si—NMR (ppm): 8 (—Si(CH$_3$)$_3$), −22 (O—Si(CH$_3$)$_2$—).

Comparative Example 2 (CEx. 2)

A silicone-hydrogel film was obtained in the same way as in Example 3 except that the compound obtained in Comparative Example 1 was used instead of compound obtained in Example 1. The clear, transparent thin film produced was stored in pure water and measured for the properties.

Hydrolytic stability of the monomer of the present invention was measured using HPLC (US 20100069279). 0.5 wt % of the monomers obtained in Example 1 (Ex.1) is introduced into three different vials containing 6.5, 7 and 7.5 pH solutions. The vials were sealed with leak proof seal and heated to 85 deg C. The heat accelerated hydrolytic degradation composition changes was monitored using HPLC as a function of time. In a same way, the monomer obtained in comparative example 1 was also measured for hydrolytic stability.

The monomer of the current invention (Ex.1) showed improved hydrolytic stability under acidic, basic and neutral conditions in comparison to the conventional siloxane monomer (CEx.2) over the acidic, neutral and basic pH conditions (FIG. 1).

TABLE 1

Formulation details and the properties of the silicone hydrogel films.

| Silicone hydrogel | Ex. 3 | CEx. 2 |
| --- | --- | --- |
| Composition (wt. %) | | |
| Silicone monomer (Ex 1) | 49 | — |
| Silicone monomer (CEx 1) | — | 49 |
| HEMA | 49 | 49 |
| EGDMA | 1 | 1 |
| Benzoyl peroxide | 1 | 1 |
| Properties | | |
| Equilibrium water content (%) | 27 | 30 |
| Dynamic contact angle (at 2 minutes) | 36° ± 4° | 42° ± 4° |
| Captive bubble contact angle | 43° ± 4° | 40° ± 3° |
| Young's modulus [MPa] | 0.5 ± 0.1 | 0.8 ± 0.3 |
| Oxygen permeability (Dk) [Barrer] | 347 ± 10 | 305 ± 10 |

Table 1 compares the properties of the silicone-hydrogel films produced using the monomers with carbosiloxane linkage (Ex.1) and monomer without the carbosiloxane linkage (Ex.2). The monomer, apart from the improved hydrolytic stability under different pH conditions, showed improved oxygen permeability and lower modulus in comparison to the silicone hydrogel film produced using the conventional silicone monomers.

Stern, et al (J. Polymer Science Part B: Polymer Physics 25 (1987) 1263-1298) reported that substitution of methyl groups by bulky groups (e.g., ethyl, isopropyl, butyl, hexyl) on the silicone backbone, or the replacement of siloxane (—SiOSi—) linkage by carbosilane (—Si(CH$_2$)$_n$Si—) linkage resulted in reduced oxygen permeability. Based on Stern et al report, one would expect the oxygen permeability to get reduced when siloxane linkage (—Si—O—Si) is replaced by carbosiloxane linkage (—Si(CH$_2$)$_n$Si—) in the backbone chain. Surprisingly, the silicone hydrogel film produced using the carbosiloxane monomer of the current invention showed improved oxygen permeability in comparison to the corresponding siloxane monomer having conventional siloxane linkage.

While the invention has been described with reference to a preferred embodiment, those skilled in the art will understand that various changes may be made and equivalents may be substituted for elements thereof without departing from the scope of the invention. It is intended that the invention not be limited to the particular embodiment disclosed as the best mode for carrying out this invention, but that the invention will include all embodiments falling within the scope of the appended claims. All citations referred herein are expressly incorporated herein by reference.

What is claimed is:

1. A silicone monomer comprising of at least one carbosiloxane linkage having the general formulae (I):

(R$^1$R$^2$R$^3$)—Si—Y$^1$—[Si(R$^4$R$^5$)Y$^2$)]$_a$—Si(R$^6$R$^7$)—Z  (I)

wherein a is 0 to about 100;
Y$^1$ is a substituted or unsubstituted divalent alkyl linking group of 1 to about 10 carbon atoms;
Y$^2$ is a substituted or unsubstituted divalent alkyl linking group of 1 to about 10 carbon atoms or a hetero atom;
R$^1$, R$^2$, R$^3$, R$^4$, R$^5$, R$^6$, and R$^7$ is independently selected from the group consisting of monovalent aliphatic, cycloaliphatic or aromatic or halogenated hydrocarbon groups of 1 to about 10 carbons, —Y$^2$Si(R$^8$R$^9$R$^{10}$) and A, wherein R$^8$R$^9$R$^{10}$ is independently selected from the group consisting of monovalent aliphatic, cycloaliphatic and aromatic hydrocarbon groups of 1 to about 10 carbons; A is a monovalent hydrophilic or hydrophobic moiety selected from the group consisting of substituted or unsubstituted, saturated and unsaturated aliphatic, cycloaliphatic or aromatic hydrocarbons and substituted or unsubstituted, saturated and unsaturated aliphatic, cycloaliphatic or aromatic hydrocarbons containing hetero atoms;
Z has the following general formulae (II)

R$^{11}$—B—X  (II)

wherein R$^{11}$ is a linear or branched, divalent alkyl linking group having 0 to about 20 carbon atoms, B is a divalent hydrophilic or hydrophobic moiety selected from the group consisting of substituted or unsubstituted, saturated and unsaturated aliphatic, cycloaliphatic or aromatic hydrocarbons and substituted or unsubstituted, saturated and unsaturated aliphatic, cycloaliphatic or aromatic hydrocarbons containing hetero atoms, wherein B comprises a functionality chosen from an alcohol chosen from a hydroxycyclohexanyl, an ether, an ester, an amide, an amine, an acid and its salts, a cyano, a thio, a urethane, a urea, a carbonate, a carbamate, a sulfonate, a sulphonomide, a phosphate, or combinations thereof, and X is acrylamide or a polymerizable group selected from the group consisting of substituted or unsubstituted unsaturated aliphatic hydrocarbons, substituted or unsubstituted aromatic hydrocarbons, acrylates, and methacrylates.

2. The silicone monomer of claim 1, wherein R$^1$, R$^2$, R$^3$, R$^4$, R$^5$, R$^6$, R$^7$, R$^8$, R$^9$, R$^{10}$, R$^{11}$, R$^{12}$, R$^{13}$ and R$^{14}$ independently comprises a saturated monovalent hydrocarbon group of 1 to about 9 carbon atoms, a fluorinated hydrocarbon, a aralkyl or arylalkyl group, or a siloxanyl group.

3. The silicone monomer of claim 1, wherein A and B comprise at least one functional group consisting of alkyl, alcohol, ether, ester, amide, amine, acid and its salts, cyano, thio, urethane, urea, carbonate, carbamate, sulfonate, sulphonamide, and phosphate.

4. The silicone monomer of claim 1, wherein B is one of the following divalent moieties

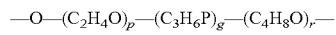

Polyether wherein p and q are independently 0 to about 100; r is 0 to about 50 and (p+q+r) is greater than 0,

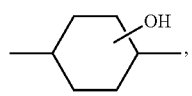

Hydroxycyclohexanyl

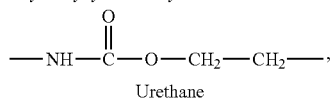

Urethane

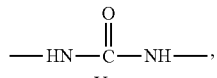

Urea

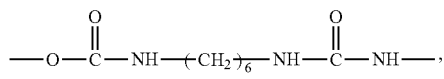

Urea and urethane

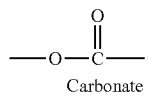 or 

Carbonate        Carbamate

5. The silicone monomer of claim 1 wherein X is acrylamide or a polymerizable moiety having the general formula (III)

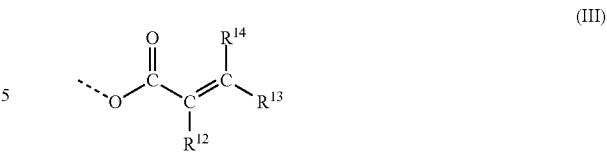

wherein $R^{12}$, $R^{13}$, and $R^{14}$ is hydrogen or a substituted or unsubstituted saturated monovalent hydrocarbon or halogenated hydrocarbon group of 1 to about 20 carbons.

6. The silicone monomer of claim 1, wherein the monomer is of the formula (IV):

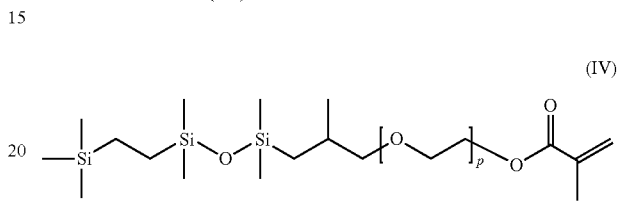

wherein p is greater than 5.

7. The silicone monomer of claim 1, wherein the monomer is of the formula (V):

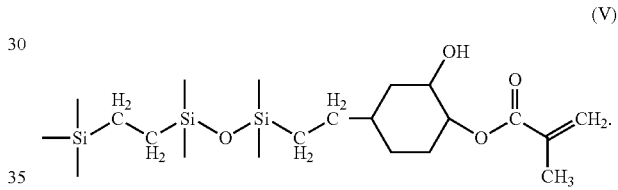

* * * * *